United States Patent
Nenadic et al.

(10) Patent No.: US 9,642,600 B2
(45) Date of Patent: May 9, 2017

(54) SHEAR WAVE ATTENUATION FROM K-SPACE ANALYSIS SYSTEM

(71) Applicant: MAYO FOUNDATION FOR MEDICAL EDUCATION AND RESEARCH, Rochester, MN (US)

(72) Inventors: Ivan Z. Nenadic, Rochester, MN (US); Shigao Chen, Rochester, MN (US); James F. Greenleaf, Rochester, MN (US); Matthew W. Urban, Rochester, MN (US); Bo Qiang, Rochester, MN (US); Heng Zhao, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/432,312

(22) PCT Filed: Sep. 30, 2013

(86) PCT No.: PCT/US2013/062617
§ 371 (c)(1),
(2) Date: Mar. 30, 2015

(87) PCT Pub. No.: WO2014/055410
PCT Pub. Date: Apr. 10, 2014

(65) Prior Publication Data
US 2015/0305719 A1    Oct. 29, 2015

Related U.S. Application Data

(60) Provisional application No. 61/708,382, filed on Oct. 1, 2012.

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC .......... *A61B 8/5223* (2013.01); *A61B 8/4483* (2013.01); *A61B 8/485* (2013.01); *G01S 7/5202* (2013.01); *G01S 7/52042* (2013.01); *G01S 15/8915* (2013.01); *G01S 7/52033* (2013.01)

(58) Field of Classification Search
CPC ....... A61B 5/055; A61B 8/5261; A61B 8/485; A61B 8/08
See application file for complete search history.

(56) References Cited

U.S. PATENT DOCUMENTS

| | | | |
|---|---|---|---|
| 6,246,895 B1 | 6/2001 | Plewes | |
| 8,469,891 B2 * | 6/2013 | Maleke | A61B 5/055 600/438 |
| 2003/0171672 A1 * | 9/2003 | Varghese | A61B 5/015 600/420 |
| 2010/0010349 A1 | 1/2010 | Park et al. | |
| 2012/0215101 A1 | 8/2012 | Maleke et al. | |

OTHER PUBLICATIONS

International Search Report and Written Opinion under date of mailing of Dec. 19, 2013, in connection with PCT/US2013/062617.

* cited by examiner

*Primary Examiner* — Joel Lamprecht
(74) *Attorney, Agent, or Firm* — Quarles & Brady LLP

(57) ABSTRACT

The present invention provides a system and method for ultrasound processes using wave attenuation derived from k-space analysis by analyzing spatial frequency domain data.

22 Claims, 6 Drawing Sheets

SHEAR WAVE ATTENUATION FROM K-SPACE ANALYSIS SYSTEM

CROSS-REFERENCE TO RELATED APPLICATIONS

This application represents the national stage entry of PCT International Patent Application PCT/US2013/062617 filed Sep. 30, 2013, which claims the benefit of U.S. Provisional Application Ser. No. 61/708,382, filed Oct. 1, 2012, the disclosures of both of the above-mentioned applications are incorporated herein by reference for all purposes.

STATEMENT REGARDING FEDERALLY SPONSORED RESEARCH

This invention was made with government support under EB002167 awarded by the National Institutes of Health. The government has certain rights in the invention.

BACKGROUND OF THE INVENTION

Tissue viscoelasticity can be imaged by monitoring shear wave propagation inside of tissue. Shear wave motion, as a function of time and space, can be analyzed in the temporal- and spatial-frequency domain by performing a Fourier transform. This domain is often called "k-space." It is known that a k-space representation of a shear wave is a useful tool for estimating shear wave velocity and applying directional filters.

The shear wave velocities, c, at different frequencies can be identified by finding the local maxima in k-space and using the temporal frequency, f, and spatial frequency, $$k = \frac{1}{\lambda},$$

coordinates, $$c = \frac{f}{k} = f\lambda,$$

where $\lambda$ is the wavelength of the shear wave. A unique feature of k-space analysis is that waves of different modes can be separated even when they are at the same frequency. This is also useful since multiple modes can exist simultaneously when tissue vibrates.

One important advantage of k-space analysis is that the waves propagating in opposite directions can be differentiated. This is especially useful in mechanical-wave-based tissue elastography methods, since wave reflections can be common in certain tissues. In fact, directional filtering is based on this feature because it only selects the energy in specific locations in k-space and then transform back to time and spatial domain, to remove waves travelling in unwanted directions.

Though, as addressed above, k-space analysis for estimating wave velocity is a useful tool, the accuracy of the estimates can vary. For example, soft tissues are inherently viscoelastic. Thus, as waves travel through soft tissues, the energy in the wave is diminished, causing its amplitude to decrease. Without a more accurate complex modulus of the tissue, velocity estimates are of limited clinical utility.

Therefore, it would be desirable to have a system and method for determining a complex modulus of the tissue that can be used in clinical analysis of tissue.

SUMMARY OF THE INVENTION

The present invention overcomes the aforementioned drawbacks by providing a system and method for estimating shear wave attenuation from k-space analysis. By estimating tissue attenuation, a more accurate calculation of the complex modulus of the tissue can be performed, which can then be used in clinical analysis and diagnosis.

In accordance with one aspect of the present invention, a system is disclosed for determining a property of a tissue of a subject. The system includes an ultrasound transmitter configured to engage a subject and cause a shear wave to propagate through the subject and an ultrasound receiver configured to acquire data from the subject as the shear wave to propagates through the subject. The system also includes a processor configured to transform the data acquired by the ultrasound receiver into a frequency domain to form k-space data and analyze the k-space data to determine an attenuation of the shear wave as it propagated through the subject. The system also includes a report generator configured to generate a report indicating at least one of the attenuation of the shear wave as it propagated through the subject and a metric calculated using the attenuation of the shear wave as it propagated through the subject.

In accordance with another aspect of the present invention, a system is disclosed for determining a property of a tissue of a subject. The system includes an ultrasound transmitter configured to engage a subject and cause a shear wave to propagate through the subject and an ultrasound receiver configured to acquire data from the subject as the shear wave to propagates through the subject. The system also includes a processor configured to transform the data acquired by the ultrasound receiver into a frequency domain to form k-space data and analyze the k-space data to determine a magnitude of the k-space data to identify a peak magnitude. The processor is further configured to use the magnitude profile of the k-space data to determine an attenuation of the shear wave as it propagated through the subject and calculate at least one property of the tissue using the attenuation of the shear wave as it propagated through the subject. The processor is also configured to generate a report indicating at least the at least one property of the tissue.

In accordance with yet another aspect of the present invention, a method is disclosed for estimating at least one of phase velocity and attenuation of shear waves propagating through a subject. The method includes controlling a source of energy to generate shear waves within the subject and acquiring, with a medical device, data about the shear waves as the shear waves propagate through the subject. The method also includes transforming the data to a frequency domain to form k-space data, analyze the k-space data to determine at least one of an attenuation and a velocity of the shear wave as it propagated through the subject, and generating a report using the at least one of the attenuation and the velocity of the shear wave as it propagated through the subject.

The foregoing and other aspects and advantages of the invention will appear from the following description. In the description, reference is made to the accompanying drawings which form a part hereof, and in which there is shown by way of illustration a preferred embodiment of the inven-

DETAILED DESCRIPTION OF THE INVENTION

Figure 1:
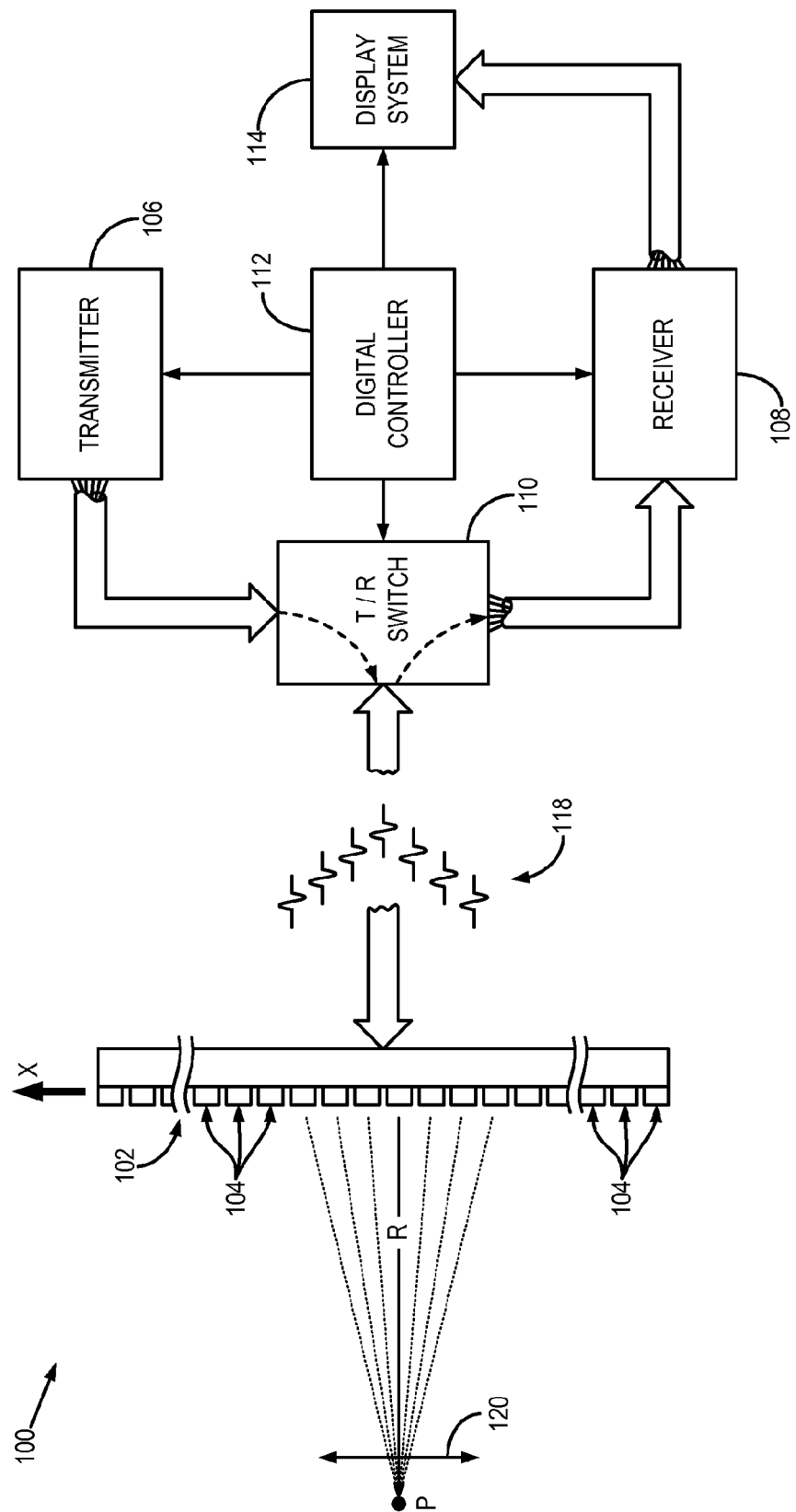
FIG. 1 is a block diagram of an ultrasound system for use with the present invention.

Referring to FIG. 1, an ultrasonic imaging system 100 includes a transducer array 102 containing a plurality of separately driven elements 104 that each produce a burst of ultrasonic energy when energized by a pulse produced by a transmitter 106. The ultrasonic energy reflected back to the transducer array 102 from the tissue of interest is converted to an electrical signal by each transducer element 104 and applied separately to a receiver 108 through a set of switches 110. The transmitter 106, receiver 108, and the switches 110 are operated under the control of a digital controller 112 responsive to the commands input by the human operator. A complete scan is performed by acquiring a series of echoes in which the switches 110 are set to their transmit position, the transmitter 106 is gated on momentarily to energize each transducer element 104, the switches 110 are then set to their receive position, and the subsequent echo signals produced by each transducer element 104 are applied to the receiver 108. The separate echo signals from each transducer element 104 are combined in the receiver 108 to produce a single echo signal which is employed to produce a line in an image on a display system 114.

The transmitter 106 drives the transducer array 102 such that an ultrasonic beam is produced which is directed substantially perpendicular to its front surface. To focus this beam at a range, R, from the transducer 102 a subgroup of the elements 104 are energized to produce the beam, and the pulsing of the inner elements 104 in this subgroup are delayed relative to the outer elements 104 as shown at 118. A beam focused at point P results from the interference of the small separate wavelets produced by the subgroup elements. The time delays determine the depth of focus, or range R, and this is typically changed during a scan when a two-dimensional image is to be produced. The same time delay pattern is used when receiving the echo signals resulting in dynamic focusing of the echo signals received by the subgroup of elements 104. In this manner a single scan line in the image is formed.

To generate the next scan line, the subgroup of elements to be energized are shifted one element position along the transducer length and another scan line is required. As indicated by the arrow 120, the focal point, P, of the ultrasonic beam is thus shifted along the length of the transducer 102 by repeatedly shifting the location of the energized subgroup of elements 104.

Figure 2:
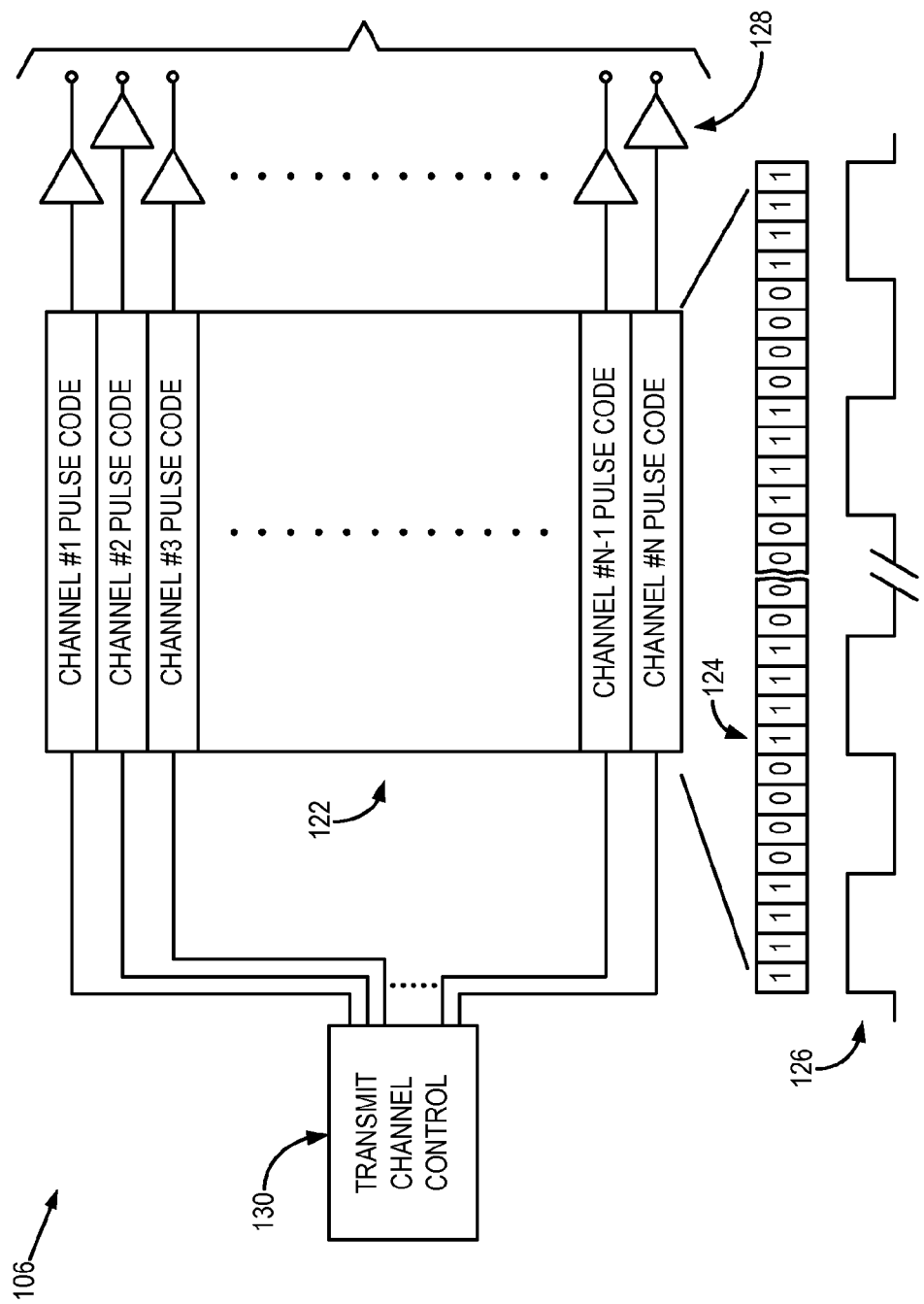
FIG. 2 is a block diagram of a transmitter which forms part of the ultrasound system of FIG. 1.

Referring particularly to FIG. 2, the transmitter 106 includes a set of channel pulse code memories which are indicated collectively at 122. Each pulse code memory 122 stores a bit pattern 124 that determines the frequency of the ultrasonic pulse 126 that is to be produced. This bit pattern is read out of each pulse code memory 122 by a master clock and applied to a driver 128 which amplifies the signal to a power level suitable for driving the transducer 102 of FIG. 1. In the example shown in FIG. 2, the bit pattern is a sequence of four "1" bits alternated with four "0" bits to produce a 5 megahertz ("MHz") ultrasonic pulse 126. The transducer elements 104 of FIG. 1 to which these ultrasonic pulses 126 are applied respond by producing ultrasonic energy.

As indicated above, to steer the transmitted beam of the ultrasonic energy in the desired manner, the pulses 126 for each of the N channels must be produced and delayed by the proper amount. These delays are provided by a transmit control 130 which receives control signals from the digital controller 112 of FIG. 1. When the control signal is received, the transmit control 130 gates a clock signal through to the first transmit channel 122. At each successive delay time interval thereafter, the clock signal is gated through to the next channel pulse code memory until all the channels to be energized are producing their ultrasonic pulses 126. Each transmit channel 122 is reset after its entire bit pattern 124 has been transmitted and the transmitter 106 then waits for the next control signal from the digital controller 112 of FIG. 1. By operating the transmitter 106 in this manner, ultrasonic energy can be focused on a focal point, P, when practicing the herein described method. This focal point can be steered electronically with the appropriate changes to the timing delays provided by the transmit control 130. The term "focal point," as referred to herein, includes not only a single point object in the usual sense, but also a general region-of-interest to which ultrasound energy is delivered in a substantially focused manner.

Figure 3:
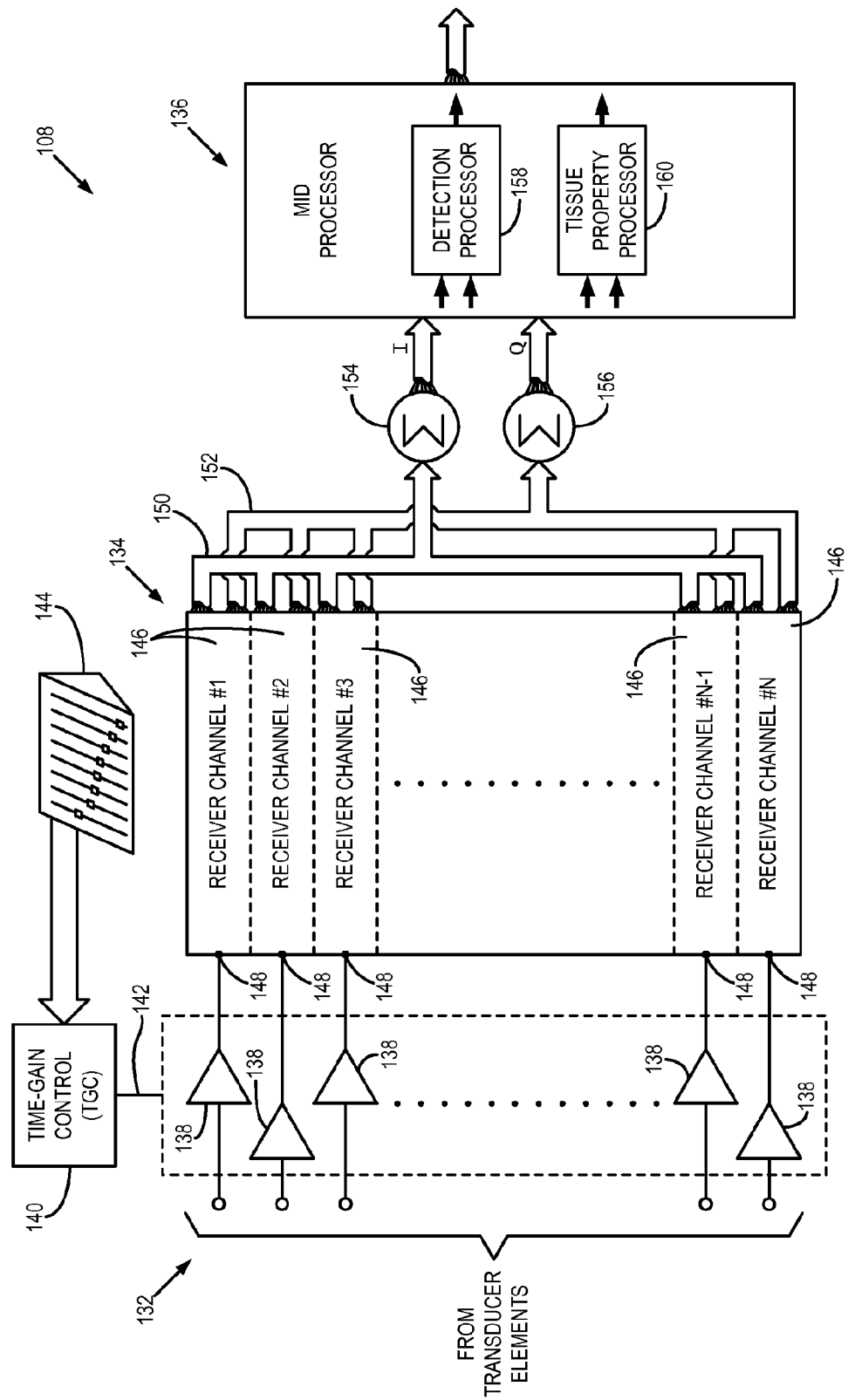
FIG. 3 is a block diagram of a receiver which forms part of the ultrasound system of FIG. 1.

Referring particularly to FIG. 3, the receiver 108 is comprised of three sections: a time-gain control ("TGC") section 132, a beam forming section 134, and a mid processor 136. The time-gain control section 132 includes an amplifier 138 for each of the N receiver channels and a time-gain control circuit 140. The input of each amplifier 138 is connected to a respective one of the transducer elements 104 of FIG. 1 to receive and amplify the echo signal which it receives. The amount of amplification provided by the amplifiers 138 is controlled through a control line 142 that is driven by the time-gain control circuit 140. As the range of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by the operator who manually sets TGC linear potentiometers 144 to values which provide a relatively uniform brightness over the entire range of the scan. The time interval over which the echo signal is acquired determines the range from which it emanates, and this time interval is divided into segments by the TGC control circuit 140. The settings of the potentiometers are employed to set the gain of the amplifiers 138 during each of the respective time intervals so that the echo signal is amplified in ever increasing amounts over the acquisition time interval.

The beam forming section 134 of the receiver 108 of FIG. 1 includes N separate receiver channels 146. Each receiver channel 146 receives the analog echo signal from one of the TGC amplifiers 138 at an input 148, and it produces a stream of digitized output values on an I bus 150 and a Q bus 152. Each of these I and Q values represents a sample of the echo signal envelope at a specific range, R. These samples have been delayed in the manner described above such that when they are summed at summing points 154 and 156 with the I and Q samples from each of the other receiver channels 146, they indicate the magnitude and phase of the echo signal reflected from a point, P, located at range, R, on the ultrasonic beam.

Referring still to FIG. 3, the mid processor section 136 receives the beam samples from the summing points 154 and 156. The I and Q values of each beam sample is a digital number which represents the in-phase and quadrature components of the magnitude of the reflected sound from a point, P. The mid processor 136 can perform a variety of calculations on these beam samples, where choice is determined by the type of image to be reconstructed. For example, if a conventional magnitude image is to be produced, a detection processor indicated at 158 is implemented in which a digital magnitude, M, is calculated from each beam sample according to $M=\sqrt{I^2+Q^2}$ and output to the display system 114 of FIG. 1 or intermediate processing systems.

The detection processor 158 may also implement correction methods that, for example, examine the received beam samples and calculate corrective values that can be used in subsequent measurements by the transmitter 106 and receiver 108 of FIG. 1 to improve beam focusing and steering. Such corrections are desirable, for example, to account for the non-homogeneity of the media through which the sound from each transducer element travels during a scan.

The present invention may be implemented, in part, by a tissue property processor 160 that forms part of the mid-processor 136. As will be explained in detail below, this processor 160 receives the I and Q beam samples acquired during a sequence of measurements of the subject tissue and calculates a mechanical property of the tissue.

Figure 4:
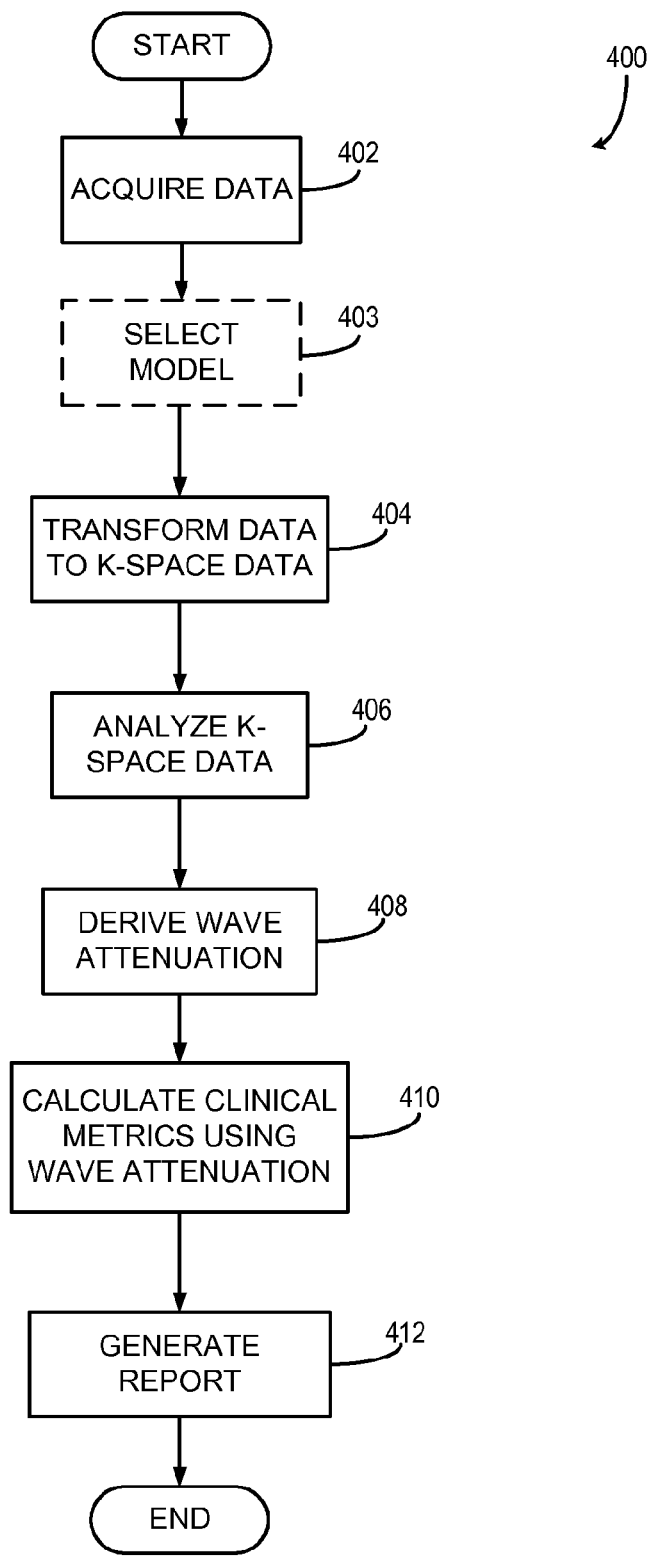
FIG. 4 is a flow chart setting forth the steps of a method in accordance with the present invention.

Referring to FIG. 4, in accordance with the present invention, tissue viscoelasticity can be imaged by monitoring shear wave propagation inside of tissue. The steps 400 of a process starts at process block 402 with the acquisition of data using a medical imaging system, for example, an ultrasound system such as described above with respect to FIGS. 1-3. As mentioned, shear wave motion as a function of time and space can be analyzed in the temporal- and spatial-frequency domain by performing a Fourier transform. This domain is often called k-space.

At optional process block 403, a model for the shear wave motion may be selected and at process block 404, the acquired data is transformed to k-space data. That is, as will be described, the shear wave may be considered to be planar, cylindrical, spherical, or any of a variety of other geometries. As an example, consider a source free, one-dimensional, plane, shear wave propagating in a linear viscoelastic medium that is described by:

$$\frac{\partial^2 u}{\partial t^2} - \frac{G^*}{\rho}\frac{\partial^2 u}{\partial x^2} = 0, ; \quad \text{(Eq. 1)}$$

where u is the displacement, x and t are the spatial and time variables, respectively. $G^*$ is the complex shear modulus and $\rho$ is the mass density.

The general solution to equation 1 is:

$$u(x,t) = u_0 e^{j(\omega_0 t + k^*_0 x)}, \quad \text{(Eq. 2);}$$

where $\omega_0 = 2\pi f_0$ is the angular frequency and $f_0$ is the frequency, of the wave. $u_0$ is the initial amplitude of the wave. The complex wave number $k^*_0$ can be expressed in terms of angular frequency $\omega_0$, wave speed c and attenuation $\alpha(>0)$ as:

$$k^*_0 = \frac{\omega_0}{c} + j\alpha .. \quad \text{(Eq. 3)}$$

Combining equation 2 and equation 3 gives:

$$u(x,t) = u_0 e^{j(\omega_0 t + k^*_0 x)} = u_0 \left[ e^{-\alpha x} e^{j\omega_0 \frac{x}{c}} \right] \left[ e^{j\omega_0 t} \right], . \quad \text{(Eq. 4)}$$

Transforming u(x,t) to k-space by taking 2D Fourier transform gives:

$$U(k,f) = \int_{-\infty}^{\infty}\int_{-\infty}^{\infty} u(x,t) e^{-j2\pi(kx+ft)} dx dt, ; \quad \text{(Eq. 5)}$$

where k and f are the wave number and frequency variables, respectively, both of which are real. Since the two parts with x and t in equation 4 are separable, equation 5 can be simplified to:

$$U(k,f) = u_0 \times FT_t\{e^{j\omega_0 t}\} \times FT_x\left\{e^{-\alpha x} e^{j\omega_0 \frac{x}{c}}\right\}, ; \quad \text{(Eq. 6)}$$

where $FT_t\{\bullet\}$ and $FT_x\{\bullet\}$ are 1D Fourier transforms applied to time and spatial domains, respectively. They are defined as:

$$FT_t\{g(t)\} = \int_{-\infty}^{\infty} g(t) e^{-j2\pi ft} dt;; \quad \text{(Eq. 7)}$$

$$FT_x\{h(x)\} = \int_{-\infty}^{\infty} h(x) e^{-j2\pi kx} dx .. \quad \text{(Eq. 8)}$$

Note that:

$$FT_t\{e^{j\omega_0 t}\} = \delta(f - f_0), ; \quad \text{(Eq. 9)}$$

$$FT_x\left\{e^{-\alpha x} e^{j\omega_0 \frac{x}{c}}\right\} = \frac{1}{\alpha + j2\pi k} \otimes \delta\left(k - \frac{f_0}{c}\right) = \frac{1}{\alpha + j2\pi\left(k - \frac{f_0}{c}\right)}, ; \quad \text{(Eq. 10)}$$

where $\delta(\bullet)$ is the Dirac delta function. Substituting the corresponding parts in Eq. 6 with Eq. 9 and Eq. 10 gives:

$$U(k, f) = \frac{u_0 \delta(f - f_0)}{\alpha + j2\pi\left(k - \frac{f_0}{c}\right)} \quad (\text{Eq. 11})$$

The magnitude can be expressed as:

$$|U(k, f)| = \frac{u_0 \delta(f - f_0)}{\sqrt{\alpha^2 + 4\pi^2\left(k - \frac{f_0}{c}\right)^2}} \quad (\text{Eq. 12})$$

Eq. 12 shows that for a wave with frequency $f_0$, the magnitude of its k-space transform has a corresponding peak at $(k,f)=(f_0/c, f_0)$. Thus, the present invention recognizes that such k-space analysis can be used to calculate wave velocity. Hence, at process block 406, the k-space data is analyzed, for example to calculate wave velocity.

At process block 408, wave attention is derived from the k-space analysis. In particular, practically, $\delta(0)$ has a finite amplitude. As such, it can be denoted as $\hat{\delta}(0)$ and $u_0 \hat{\delta}(0)$ can be defined as $u_0 \hat{\delta}(0) \equiv 2A$, where:

$$|U(k, f)|_{f=f_0} = |U(k, f_0)| = \frac{2A}{\sqrt{\alpha^2 + 4\pi^2\left(k - \frac{f_0}{c}\right)^2}} \quad (\text{Eq. 13})$$

Its maximum magnitude is:

$$|U(k, f_0)|_{max} = \left|U\left(\frac{f_0}{c}, f_0\right)\right| = \frac{2A}{\alpha} \quad (\text{Eq. 14})$$

At half maximum magnitude:

$$\frac{2A}{\sqrt{\alpha^2 + 4\pi^2\left(k - \frac{f_0}{c}\right)^2}} = \frac{|U(k, f_0)|_{max}}{2} = \frac{A}{\alpha} \quad (\text{Eq. 15})$$

Solving for k, the two solutions are:

$$k_{1,2} = \pm\frac{\sqrt{3}}{2\pi}\alpha - \frac{\omega_0}{c} \quad (\text{Eq. 16})$$

Therefore, the full width at half maximum (FWHM) is:

$$FWHM = |k_1 - k_2| = \frac{\sqrt{3}}{\pi}\alpha \quad (\text{Eq. 17})$$

With this in mind, wave attenuation can then be estimated as:

$$\alpha = \frac{FWHM \times \pi}{\sqrt{3}} \quad (\text{Eq. 18})$$

For some ultrasound elastography methods, the particle velocity instead of displacement may be used as the raw measurement for this determination. The particle velocity is the time derivative of the displacement, so the differentiation property of Fourier transform can be applied. Equation 18 still holds in this case.

After attenuation is derived at process bock 408, a variety of additional calculations or determinations can be performed at process block 410, for example, to provide clinically-useful information and/or provide clinical report, such as indicated at process block 412. For example, complex wave number $k^*_0$ can be calculated using equation 3 above and/or the material complex shear modulus can be estimated as:

$$G^* = \rho\left(\frac{\omega_0}{k_0^*}\right)^2. \quad (\text{Eq. 19})$$

Both wave number and shear modulus can be used to, for example, improve the performance of tissue elastography. In this regard, the report generated at process block 412 may include an elastography or report indicating the elastic properties of tissue.

Validation

Figure 5:
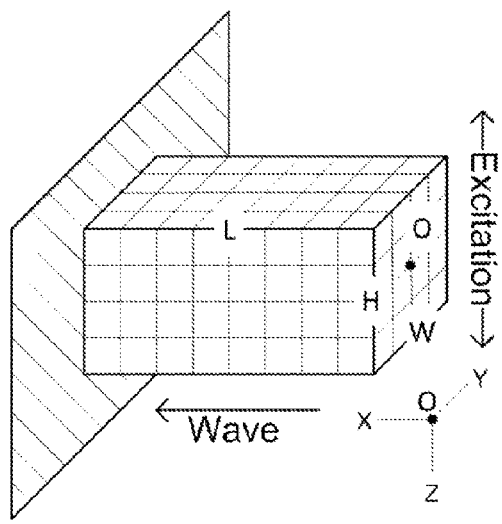
FIG. 5 is a graphic representation of a configuration of a finite element model, where displacement excitation is applied to the right surface of the model while the left surface is fixed and displacement in z direction of each node in the y=z=0 line is extracted and processed.

A 3D FE model was constructed in Abaqus/CAE 6.10-EF1 (Dassault Systèmes Simulia Corp., Providence, R.I., USA), as shown in FIG. 5. The size of the model is $L \times W \times H = 100 \times 50 \times 50$ mm$^3$. The model was meshed with 2,000,000 8-node linear elements with reduced integration and hourglass control (C3D8R). The size of the each element is $0.5 \times 0.5 \times 0.5$ mm$^3$. A displacement excitation was applied to the x=0 surface of the model. Two different kinds of waveforms were tested for the excitation: tone burst and impulse. For the tone burst excitations, their frequencies were 100 to 500 Hz with 50 Hz separations and their peak-to-peak amplitudes were 20 μm. Each tone burst lasted 10 ms. For the impulse excitation, the duration of the pulse was 100 μs and its amplitude was 20 μm. For both excitations, the total simulated time was 100 ms and temporal step was 0.1 ms. Displacement in z direction was extracted along the line y=z=0, as denoted in FIG. 5. Along that line, a pure plane shear wave was generated.

The medium of the model was assumed to be a Voigt material, which is described further below. A Voigt material was used because it is experimentally approved to provide a simple and effective way to describe shear wave speed and attenuation in tissue. Its material properties are listed as below: shear elasticity, $\mu_1 = 5$ kPa, shear viscosity, $\mu_2 = 5$ Pa·s, mass density $\rho = 1000$ kg/m$^3$, Poisson's ratio v=0.4999. The value of $\mu_1$ and $\mu_2$ are chosen because they are in the physical range of soft tissues. For example, skin ($\mu_1 = 2-50$ kPa, $\mu_2 = 2-40$ Pa·s), muscle ($\mu_1 = 5-12$ kPa, $\mu_2 = 1-4$ Pa·s) [20] and liver ($\mu_1 = 2-8$ kPa, $\mu_2 = 0.5-5$ Pa·s). The theoretical shear wave speed $c_s$ and attenuation $\alpha_s$ were calculated as:

$$c_s = \sqrt{\frac{2(\mu_1^2 + \omega^2\mu_2^2)}{\rho\left(\sqrt{\mu_1^2 + \omega^2\mu_2^2} + \mu_1\right)}}, \quad (\text{Eq. 20});$$

and $$\alpha_s = \sqrt{\frac{\rho\omega^2\left(\sqrt{\mu_1^2 + \omega^2\mu_2^2} - \mu_1\right)}{2(\mu_1^2 + \omega^2\mu_2^2)}}. \quad (\text{Eq. 21}).$$

Figure 6:
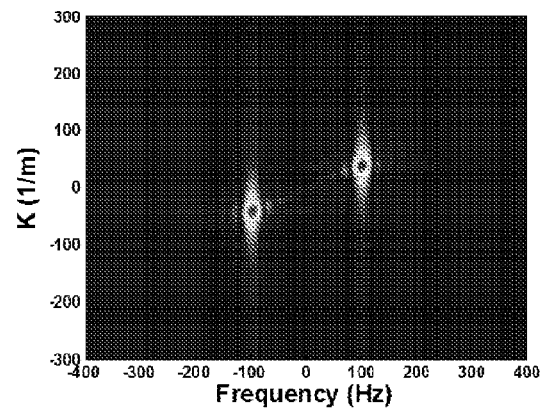
FIG. 6 is a set of corresponding graphs showing k-space representation for tone burst excitation=100 Hz and illustrating that locations of peaks can be used to calculate wave speed and the full width, half maximum (FWHM) calculations can be used to estimate wave attenuation.
Figure 6:
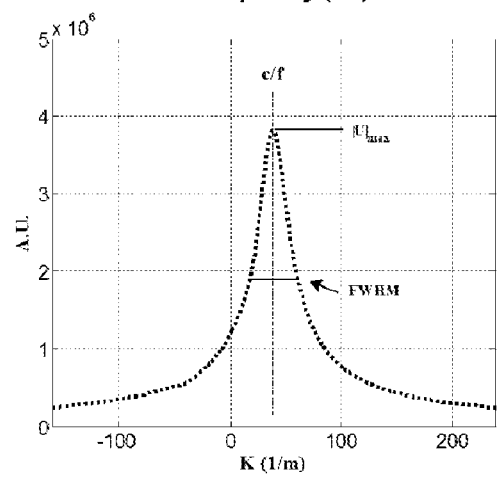
Figure 7:
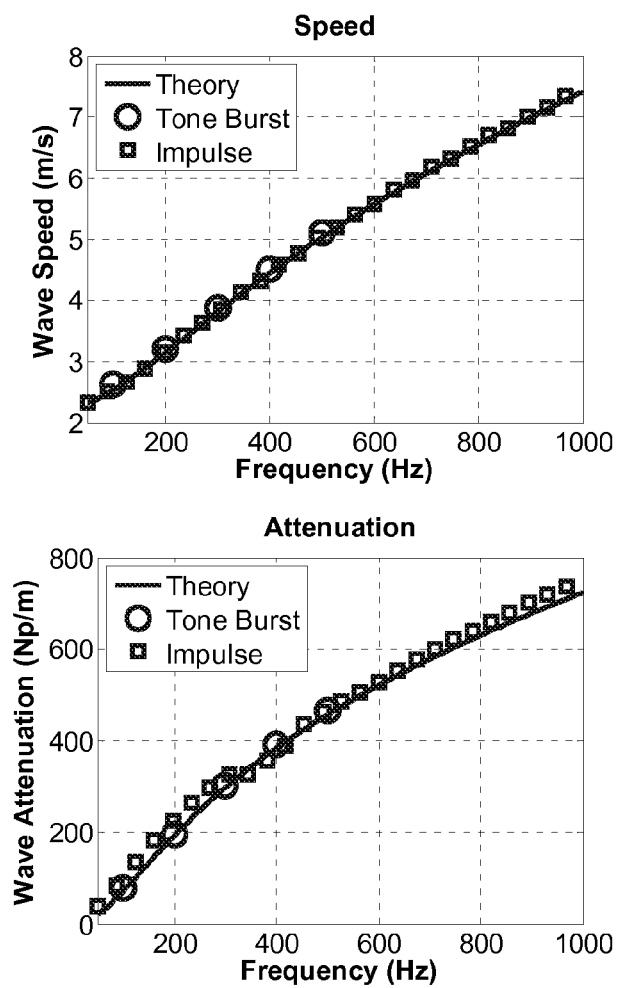
FIG. 7 is a set of graphs of wave speed and attenuation estimated from the tone burst and impulse simulations, in comparison with theoretical values.

FIG. 6 shows a representative k-space transform obtained by 2D FFT for a tone burst excitation at 100 Hz. In this case, the particle velocity values at each node were used in the computation. The magnitude profile at the excitation frequency is plotted in FIG. 6. The peak location and pulse width were used to calculate wave speed and attenuation, respectively. FIG. 7 is a set of graphs that compare estimated shear wave speeds and attenuations for both tone burst and impulse excitations. The results show that, for both excitation types, the estimations matched the theoretical speeds and attenuations.

Discussions

For a plane wave, the estimated attenuation by equation 18 comes only from material. In the case of cylindrical or spherical waves, geometric attenuation could be considered. Compensation for this geometric attenuation can be done by using the appropriate wave equations and applying a Fourier transform to their general solutions for each different wave type.

In case of cylindrical and spherical waves, the motion (or velocity, or acceleration) field has to be corrected by a factor of $\sqrt{r}$ or r, where r is the distance vector. Here, we show the correction factor for the case of a cylindrical wave. Shear motion ($u_z$) along the axis of excitation (z-axis) in case of a cylindrical wave is defined as:

$$u_z(r, t) = \frac{j}{4} H_0^{(1)}(k_0^* r) e^{-j\omega t}; \quad (Eq.\ 22)$$

where r is distance from the excitation, t is time, H a Hankel function and $k_0^*$ the complex wave number. In case of $k_0^* r \gg 0$, the equation simplifies into:

$$u_z(r, t)_{@k_0^* r \gg 0} = \frac{i}{4} \sqrt{\frac{2}{\pi k_0^* r}} e^{i(k_0^* r - \omega t)}. \quad (Eq.\ 23)$$

It should be noted that except for $1/\sqrt{r}$, all other terms are constants and constants do not affect the shape of the k-space and only scale it by a factor. Thus, multiplying both sides of $u_z$ by $\sqrt{r}$, results in Eq. 3, where the right-hand side is equal to the plane wave motion multiplied for a constant, as follows:

$$\sqrt{r} \cdot u_z(r, t)_{@k_0^* r \gg 0} = \frac{i}{4} \sqrt{\frac{2}{\pi k_0^*}} e^{i(k_0^* r - \omega t)}; \quad (Eq.\ 24)$$

$$\sqrt{r} \cdot u_z(r, t)_{@k_0^* r \gg 0} = (Const) e^{i(k_0^* r - \omega t)}. \quad (Eq.\ 25)$$

A similar process can be performed for spherical waves with a factor of r instead of $\sqrt{r}$ used for the cylindrical waves. Performing a 2D Fourier transform on Eq. 24 results in the same expression as in Eq. 4, except that $u_0$ is multiplied by a constant, which does not change the shape of the peak in k-space so the velocity and attenuation measurements are invariant. A combination of the corrections for cylindrical and spherical waves, or a modification of either of them, can be used to account for propagations that are any mixture of plane, cylindrical and spherical waves.

It is worth-mentioning again that one of the advantages of k-space analysis, compared to some other methods for wave speed and attenuation estimation, such as phase and amplitude gradient methods, lies in its robustness to wave reflections. As shown in FIG. 6, waves travelling in the positive direction have energy concentrated in the first and third quadrants of k-space. It can be shown that waves travelling in the opposite direction will have energy peaks only in the second and fourth quadrants. Therefore, k-space analysis can differentiate the waves in the desired direction from the reflected waves.

A practical issue in performing a Fourier transform on sampled data is the length of the FFT. Normally, zero padding can be used to increase the resolution in the k-space domain. The present invention has verified that the proposed method is not affected by the number of points used in the Fourier transforms in both dimensions. Another issue related to Fourier transform is windowing. Applying a window modifies the energy distribution in time or spatial domain; it will affect the wave attenuation estimation, although wave speed estimation remains accurate.

Thus, the present invention provides a system and method for ultrasound processes and analysis for estimating wave attenuation using k-space analysis. The present invention, by using k-space analysis, provides improved robustness to wave reflections, since after Fourier transform, the reflected waves will appear in different quadrants from the waves of interest. Attenuation estimations in accordance with the present invention are not affected by zero padding in Fourier transform but will be biased if windowing is applied. Tests show that for tone burst and impulse excitations, the estimated wave speed and attenuation values match the expectations. While the foregoing descriptions were made with respect to plane wave, it can be extended to others, such as cylindrical and spherical waves, for example.

Any of the foregoing methods, processes, and steps may be embodied as systems or methods or computer-implemented processes. Thus, the foregoing may be performed by computer processors that are configured or have access to a computer-readable, non-transitory storage medium having instructions stored thereon. Whether direction configured or caused to when accessing the instructions, the computer processors may carry out the foregoing. The processor may be one of the above-described processors, for example, as described with respect to FIGS. 1-3.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for determining a property of a tissue of a subject, the system comprising:
    an ultrasound transmitter configured to engage a subject and cause a shear wave to propagate through the subject;
    an ultrasound receiver configured to acquire data from the subject as the shear wave to propagates through the subject;
    a processor configured to:
        transform the data acquired by the ultrasound receiver into a spatial frequency domain to form k-space data;
        analyze the k-space data to determine an attenuation of the shear wave as it propagated through the subject; and
    a report generator configured to generate a report indicating at least one of the attenuation of the shear wave as it propagated through the subject and a metric calculated using the attenuation of the shear wave as it propagated through the subject.

2. The system of claim 1 wherein the processor is configured to analyze a magnitude of the k-space data to identify a peak magnitude and use the magnitude profile of the k-space data to determine the attenuation of the shear wave.

3. The system of claim 2 wherein the processor is configured to determine a frequency, $f_0$, of the shear wave and analyze the magnitude of the k-space data to identify the peak magnitude at $(k,f)=(f_0/c,f_0)$, wherein k is a wave number variable and f is frequency variable associated with the shear wave, and c is the wave speed of the shear wave.

4. The system of claim 2 wherein the processor is further configured to determine the attenuation of the shear wave as:

$$\alpha = \frac{FWHM \times \pi}{\sqrt{3}};$$

where $\alpha$ is the attenuation of the shear wave and FWHM is a full width at half maximum (FWHM) calculated relative to the peak magnitude.

5. The system of claim 1 wherein the processor is configured to treat the shear wave as a one-dimensional, plane, shear wave propagating in a linear viscoelastic medium.

6. The system of claim 5 wherein the one-dimensional, plane, shear wave propagating in the linear viscoelastic medium is described by:

$$\frac{\partial^2 u}{\partial t^2} - \frac{G^*}{\rho}\frac{\partial^2 u}{\partial x^2} = 0;$$

where u is a displacement of tissue by caused by the shear wave, x and t are spatial and time variables, respectively, $G^*$ is a complex shear modulus, and $\rho$ is a mass density of the tissue.

7. The system of claim 1 wherein the processor is configured to model the shear wave propagating by:

$$u(x,t) = u_0 e^{j(\omega_0 t + k_0^* x)} = u_0 \left[ e^{-\alpha x} e^{j\omega_0 \frac{x}{c}} \right]\left[ e^{j\omega_0 t} \right];$$

where $u(x, t)$ is a displacement of tissue by caused by the shear wave with spatial variable, x, and time variable, t, $u_0$ is the initial amplitude of the shear wave, $\omega_0=2\pi f_0$ is the angular frequency and $f_0$ is the frequency of the shear wave, $k_0^*$ is the complex wave number of the shear wave, $\alpha$ is the attenuation of the shear wave, and c is the wave speed of the shear wave.

8. The system of claim 6 wherein the processor is configured to transform the data acquired by the ultrasound receiver into the spatial frequency domain to form k-space data by transforming $u(x,t)$ to k-space using two-dimensional (2D) Fourier transform to derive:

$$U(k,f) = \int_{-\infty}^{\infty}\int_{-\infty}^{\infty} u(x,t)e^{-j2\pi(kx+ft)}\,dx\,dt;$$

where k and f are the wave number and frequency variables, respectively, both of which are real.

9. The system of claim 1 wherein the processor is further configured to calculate a material complex shear modulus, $G^*$, as:

$$G^* = \rho\left(\frac{\omega_0}{k_0^*}\right)^2$$

where $\omega_0=2\pi f_0$ is the angular frequency, $k_0^*$ is the complex wave number of the shear wave, and p is a mass density of the tissue and wherein the processor is configured to communicate the material complex shear modulus to the report generator to be included in the report.

10. The system of claim 1 wherein the ultrasound transducer and receiver are part of an ultrasound system configured to perform a ultrasound elastography study.

11. A system for determining a property of a tissue of a subject, the system comprising:
an ultrasound transmitter configured to engage a subject and cause a shear wave to propagate through the subject;
an ultrasound receiver configured to acquire data from the subject as the shear wave to propagates through the subject;
a processor configured to:
transform the data acquired by the ultrasound receiver into a spatial frequency domain to form k-space data;
analyze the k-space data to determine a magnitude of the k-space data to identify a peak magnitude;
using the magnitude profile of the k-space data, determine an attenuation of the shear wave as it propagated through the subject; and
calculate at least one property of the tissue using the attenuation of the shear wave as it propagated through the subject; and
generate a report indicating at least the at least one property of the tissue.

12. The system of claim 11 wherein the processor is configured to determine a frequency, $f_0$, of the shear wave and analyze the magnitude of the k-space data to identify the peak magnitude at $(k,f)=(f_0/c,f_0)$, wherein k is a wave number variable and f is frequency variable associated with the shear wave, and c is the wave speed of the shear wave.

13. The system of claim 12 wherein the processor is further configured to determine the attenuation of the shear wave as:

$$\alpha = \frac{FWHM \times \pi}{\sqrt{3}};$$

where $\alpha$ is the attenuation of the shear wave and FWHM is a full width at half maximum (FWHM) calculated relative to the peak magnitude.

14. The system of claim 11 wherein the processor is further configured to calculate a material complex shear modulus, $G^*$, as:

$$G^* = \rho\left(\frac{\omega_0}{k_0^*}\right)^2$$

where $\omega_0=2\pi f_0$ is the angular frequency, $k_0^*$ is the complex wave number of the shear wave, and p is a mass density of the tissue and wherein the processor is configured to include the material complex shear modulus in the report.

15. The system of claim 11 wherein the processor is configured to treat the shear wave as a one-dimensional, plane, shear wave propagating in a linear viscoelastic medium.

16. A method for estimating at least one of phase velocity and attenuation of shear waves propagating through a subject, the method comprising:

controlling a source of energy to generate shear waves within the subject;

acquiring, with a medical device, data about the shear waves as the shear waves propagate through the subject;

transforming the data to a spatial frequency domain to form k-space data;

analyze the k-space data to determine at least one of an attenuation and a velocity of the shear wave as it propagated through the subject; and generating a report using the at least one of the attenuation and the velocity of the shear wave as it propagated through the subject.

17. The method of claim 16 further comprising determining a frequency, $f_0$, of the shear wave and analyzing a magnitude of the k-space data to identify a peak magnitude at $(k,f)=(f_0/c,f_0)$, wherein k is a wave number variable and f is frequency variable associated with the shear wave, and c is the wave speed of the shear wave.

18. The method of claim 17 further comprising determining the attenuation of the shear wave as:

$$\alpha = \frac{FWHM \times \pi}{\sqrt{3}};$$

where $\alpha$ is the attenuation of the shear wave and FWHM is a full width at half maximum (FWHM) calculated relative to the peak magnitude.

19. The method of claim 16 further comprising calculating a material complex shear modulus, $G^*$, as:

$$G^* = \rho \left( \frac{\omega_0}{k_0^*} \right)^2$$

where $\omega_0 = 2\pi f_0$ is the angular frequency, $k_0^*$ is the complex wave number of the shear wave, and $\rho$ is a mass density of the tissue and including the material complex shear modulus in the report.

20. The method of claim 16 further comprising treating the shear wave as a one-dimensional, plane, shear wave propagating in a linear viscoelastic medium.

21. The method of claim 16 further comprising selecting a geometric model of the shear waves within the subject and applying the geometric model to the shear wave data as the shear waves propagate through the subject.

22. The method of claim 21 wherein the geometric model includes at least one of a planar, cylindrical, or spherical wave.

* * * * *